(12) United States Patent
Liu et al.

(10) Patent No.: US 9,940,735 B2
(45) Date of Patent: Apr. 10, 2018

(54) SYSTEM AND METHOD FOR GENERATING A CT SLICE IMAGE

(71) Applicant: General Electric Company, Schenectady, NY (US)

(72) Inventors: Ping Liu, Beijing (CN); Jie Wu, ChengDu (CN); Jiang Hsieh, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/185,338

(22) Filed: Jun. 17, 2016

(65) Prior Publication Data

US 2016/0371860 A1 Dec. 22, 2016

(30) Foreign Application Priority Data

Jun. 19, 2015 (CN) .......................... 2015 1 0342785

(51) Int. Cl.
*G06T 11/00* (2006.01)
*G06T 7/00* (2017.01)
(Continued)

(52) U.S. Cl.
CPC .......... *G06T 11/003* (2013.01); *G06T 7/0012* (2013.01); *G06T 7/11* (2017.01);
(Continued)

(58) Field of Classification Search
CPC ....... G06T 7/0012; G06T 7/11; G06T 11/003; G06T 2207/10081; A61B 6/025; A61B 6/03
See application file for complete search history.

(56) References Cited

U.S. PATENT DOCUMENTS

| | | | | |
|---|---|---|---|---|
| 2005/0147320 A1* | 7/2005 | Hsieh | ....................... | G06K 9/40 382/275 |
| 2006/0020200 A1* | 1/2006 | Medow | .................. | A61B 6/032 600/425 |

(Continued)

OTHER PUBLICATIONS

Jerebko et al. "Robust parametric modeling approach based on domain knowledge for computer aided detection of vertebrae column metastases in MRI." Biennial International Conference on Information Processing in Medical Imaging. Springer, Berlin, Heidelberg, 2007.*

(Continued)

*Primary Examiner* — Katrina Fujita

(57) ABSTRACT

The present invention provides a system and method for generating a CT slice image. The system comprises an MIP image generation module, a region of interest determination module, an angle setting module, a curve determination module, a match module and a slice generation module. The MIP image generation module generates MIP images of a reconstructed image; the region of interest determination module determines an image range in an original slice, and determines the parts of the MIP images within the image range as regions of interest; the angle setting module rotates the regions of interest to a plurality of specific angles for a plurality of times; the curve determination module generates a plurality of two-dimensional projected curves of the regions of interest for the plurality of specific angles; the match module selects a two-dimensional projected curve matching with a part to be diagnosed based on features of the plurality of two-dimensional projected curves; the slice generation module determines a slice position range and a slice angle based on the features of the matched curve and the corresponding specific angle.

16 Claims, 12 Drawing Sheets

(51) Int. Cl.
  *A61B 6/02* (2006.01)
  *A61B 6/03* (2006.01)
  *G06T 7/11* (2017.01)
(52) U.S. Cl.
  CPC ........... *G06T 2207/10012* (2013.01); *G06T 2207/10081* (2013.01); *G06T 2207/30196* (2013.01)

(56) References Cited

U.S. PATENT DOCUMENTS

2008/0118020 A1* 5/2008 Thibault .............. G06T 11/006
 378/4
2017/0303868 A1* 10/2017 Lee ........................ A61B 6/032

OTHER PUBLICATIONS

Vrtovec et al. "Automated curved planar reformation of 3D spine images." Physics in medicine and biology 50.19 (2005): 4527.*
Vrtovec et al. "Curved planar reformation of CT spine data." Proc. SPIE. vol. 5747. 2005.*

* cited by examiner

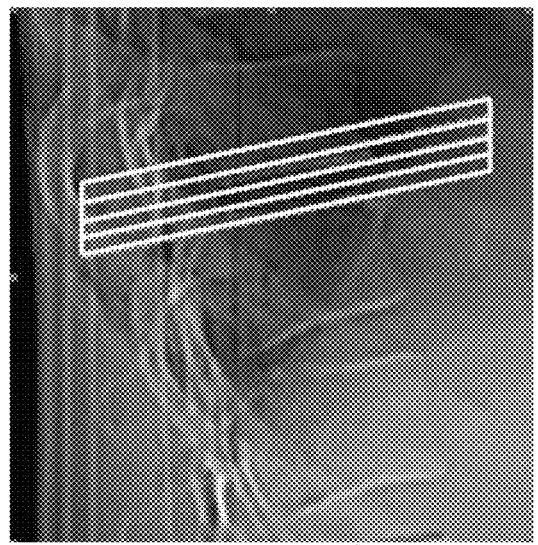
Fig. 13A
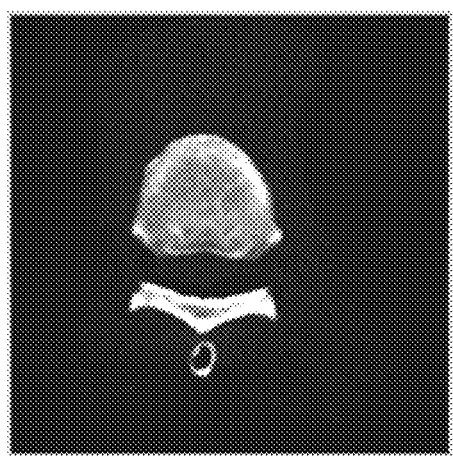 
Fig. 13B  Fig. 13C

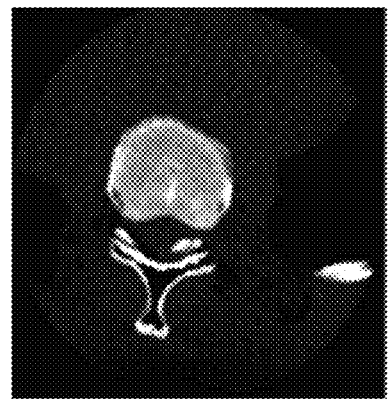 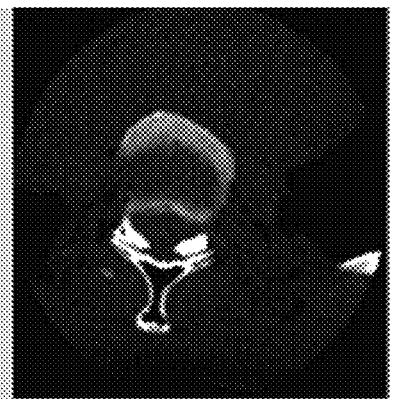
Fig. 14B             Fig. 14C
 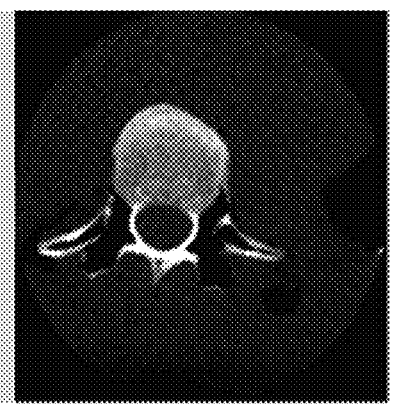
Fig. 14D             Fig. 14E

SYSTEM AND METHOD FOR GENERATING A CT SLICE IMAGE

CROSS REFERENCE TO RELATED APPLICATIONS

This application claims priority under 35 U.S.C. §§ 119(a)-(d) or (f) to prior-filed, co-pending Chinese patent application number 201510342785.5 filed Jun. 19, 2015 and titled System and method for generating a CT slice image", which is hereby incorporated by reference in its entirety.

BACKGROUND

At present, by a Computer Tomography (CT) technology, each part of the body may be diagnosed for disease. Take the lumbar intervertebral disc as an example, in order to obtain a clear intervertebral disc image, the whole lumbar is usually scanned at first to obtain a scout scan before the intervertebral disc is scanned axially. Then scanning parameters (including a scanning area, a scanning angle, etc.) are set on the scout scan for a single intervertebral disc, and axial scanning is performed based on the set scanning parameters. For a spiral scanning, an operator needs to set the posteriorly-reconstructed angle, area and the like so that the intervertebral disc can be determined from a three-dimensional image.

There exists a series of problems due to inappropriately setting parameters in the above manner that needs to preset scanning parameters or posteriorly-reconstructed parameters.

For example, for the axial scanning, after localization scanning, the operator needs to perform a very complicated inputting operation to set parameters for the axial scanning. These operations need relatively longer time, during which it is difficult for a patient to keep the posture in the localization scanning. Particularly for the elder and children, the position, angle, area and the like during the actual scanning will be very easily inconsistent with the set parameters due to posture change.

When setting parameters during the posterior reconstruction of the spiral scanning, there also exists a problem that a satisfactory image cannot be obtained due to the features such as the shape, position and the like of the part to be diagnosed or the mechanical reasons of the scanning machine itself.

Several kinds of conditions will be introduced as examples in the following in which the image obtained from the scanning cannot satisfy the clinical need.

For instance, when setting the position parameters, it is possible that due to a displacement of the position of the intervertebral disc on the Z-axis, the intervertebral disc image is not obtained just between two adjacent vertebras, and thus an image as shown in FIGS. 1A-1E are obtained. FIG. 13A shows a sagittal image of the intervertebral disc. Since the position parameters are not set appropriately, the axial scanning is performed at an upper part of the intervertebral disc so as to obtain slice images in FIGS. 13B-13E. The clinical diagnosis requires that the middle slices preferably only have soft tissue features and contain no vertebra tissue feature, while the slices at the two sides contain vertebra tissue features, which is advantageous in comparing a difference between the slice images in the middle and the slice images at the two sides to diagnose whether the intervertebral disc has pathological changes. However, the images as shown in FIGS. 13C and 13D, as the slice images in the middle, contain relatively more vertebra tissue features, but their contrast with the slice images at the two sides as shown in FIGS. 13B and 13E is relatively smaller, which is disadvantageous for the clinical diagnosis.

Moreover, as shown in FIGS. 14A-14E, since an inappropriate angle parameter is set in FIG. 14A, the middle slice images obtained in FIG. 14C contain a lower edge of an upside vertebra and the middle slice images obtained in FIG. 14D contain an upper edge of a downside vertebra, which is also disadvantageous in clinical comparison.

Furthermore, many patients' spines all have scoliosis pathological changes, as shown in FIG. 15, and there appears an angle caused by curvature of the spines at the coronal position. Since a scanning device at the utmost only supports a tilt to the head or to the foot, not supporting the tilt in other directions, a satisfactory image cannot be obtained in the axial scanning.

In addition, even if appropriate position and angle parameters are set, if the set slice thickness parameter is inappropriate, the clinical requirements still cannot be satisfied. For example, if an inappropriate thickness parameter is selected in the image as shown in FIG. 16A such that no slice images in FIGS. 16B-16E only contains soft tissue features, the requirements for the clinical diagnosis cannot be satisfied.

For the operator, it is very difficult to correct the image problems due to the above various conditions in the subsequent process, such that the image cannot satisfy the requirements of the clinical diagnosis. Therefore, the scan usually needs to be re-performed, which not only affects working efficiency, but also increases the patent's scanning dose.

Accordingly, there is a need to provide a novel system and method for generating a CT slice image, which is capable of accurately setting parameters so as to obtain a slice image satisfying the clinical requirements.

SUMMARY

Exemplary embodiments of the present invention provide a system for generating a CT slice image, comprising a maximum intensity projection (MIP) image generation module, a region of interest determination module, an angle setting module, a curve determination module, a match module and a slice generation module. The MIP image generation module is used for generating a sagittal MIP image and a coronal MIP image of a reconstructed three-dimensional image; the region of interest determination module is used for determining an image range in an original slice of the reconstructed three-dimensional image, and determining the parts of the sagittal MIP image and the coronal MIP image within the image range as a first region of interest and a second region of interest respectively; the angle setting module is used for rotating the first region of interest to a plurality of first specific angles for a plurality of times, and rotating the second region of interest to a plurality of second specific angles for a plurality of times; the curve determination module is used for generating a plurality of first two-dimensional projected curves of the first region of interest for the plurality of first specific angles, and generating a plurality of second two-dimensional projected curves of the second region of interest for the plurality of second specific angles, each first two-dimensional projected curve representing maximum CT values of columns of pixels of the first region of interest distributed along a longitudinal axis of an image on which the first region of interest resides, each second two-dimensional projected curve representing maximum CT values of columns of pixels of the second region of interest distributed along a longitudinal axis of an image on which the second region of interest resides; the match module is used for respectively selecting a first two-dimensional projected curve and a second two-dimensional projected curve matching with a part to be diagnosed based on features of the plurality of first two-dimensional projected curves and the plurality of second two-dimensional projected curves as a first matched curve and a second matched curve; the slice generation module is used for determining a slice position range and a slice angle based on the features of the first matched curve and a first specific angle corresponding to the first matched curve and based on the features of the second matched curve and a second specific angle corresponding to the second matched curve, and generating a slice in the reconstructed three-dimensional image in accordance with the determined slice position range and the determined slice angle.

Exemplary embodiments of the present invention provide a method for generating a CT slice image, comprising:

generating a sagittal MIP image and a coronal MIP image of a reconstructed three-dimensional image;

determining an image range in an original slice of the reconstructed three-dimensional image, and determining the parts of the sagittal MIP image and the coronal MIP image within the image range as a first region of interest and a second region of interest respectively;

rotating the first region of interest to a plurality of first specific angles for a plurality of times, and rotating the second region of interest to a plurality of second specific angles for a plurality of times;

generating a plurality of first two-dimensional projected curves of the first region of interest for the plurality of first specific angles, and generating a plurality of second two-dimensional projected curves of the second region of interest for the plurality of second specific angles, each first two-dimensional projected curve representing maximum CT values of columns of pixels of the first region of interest distributed along a longitudinal axis of an image on which the first region of interest resides, each second two-dimensional projected curve representing maximum CT values of columns of pixels of the second region of interest distributed along a longitudinal axis of an image on which the second region of interest resides;

respectively selecting a first two-dimensional projected curve and a second two-dimensional projected curve matching with a part to be diagnosed based on features of the plurality of first two-dimensional projected curves and the plurality of second two-dimensional projected curves as a first matched curve and a second matched curve; and determining a slice position range and a slice angle based on the features of the first matched curve and a first specific angle corresponding to the first matched curve and based on the features of the second matched curve and a second specific angle corresponding to the second matched curve, and generating a slice in the reconstructed three-dimensional image in accordance with the determined slice position range and the determined slice angle.

Other features and aspects will become apparent from the detailed description, the accompanying drawings and claims that follow.

BRIEF DESCRIPTION OF THE DRAWINGS

The present invention can be understood better in light of the description of exemplary embodiments of the present invention with reference to the accompanying drawings, in which:

FIG. 13A shows a sagittal image of an intervertebral disc, obtained in one embodiment of the present invention.

FIG. 13B shows a slice image of a disc portion with higher contrast, obtained in one embodiment of the present invention.

FIG. 13C shows a slice image with more vertebra tissue features but lower contrast, obtained in one embodiment of the present invention.

FIG. 14B shows a higher contrast image of an upside vertebra, obtained in one embodiment of the present invention.

FIG. 14C shows an image containing a lower edge of an upside vertebra, obtained in one embodiment of the present invention.

FIG. 14D shows an image containing an upper edge of a downside vertebra, obtained in one embodiment of the present invention.

FIG. 14E shows a higher contrast image of a downside vertebra, obtained in one embodiment of the present invention.

DETAILED DESCRIPTION

Hereafter, a detailed description will be given for preferred embodiments of the present invention. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical means in the art for those of ordinary skilled in the art relating to the contents disclosed in the present invention, which should not be regarded as insufficient disclosure of the present invention.

Unless defined otherwise, all the technical or scientific terms used in the Claims and the Description should have the same meanings as commonly understood by one of ordinary skilled in the art to which the present invention belongs. The terms "first", "second" and the like in the Description and the Claims of the present application for invention do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" cover the elements or objects and their equivalents illustrated following the "comprises", "comprising", "includes" and "including", but do not exclude other elements or objects. The term "coupled" or "connected" or the like is not limited to being connected physically or mechanically, nor limited to being connected directly or indirectly.

Figure 1:
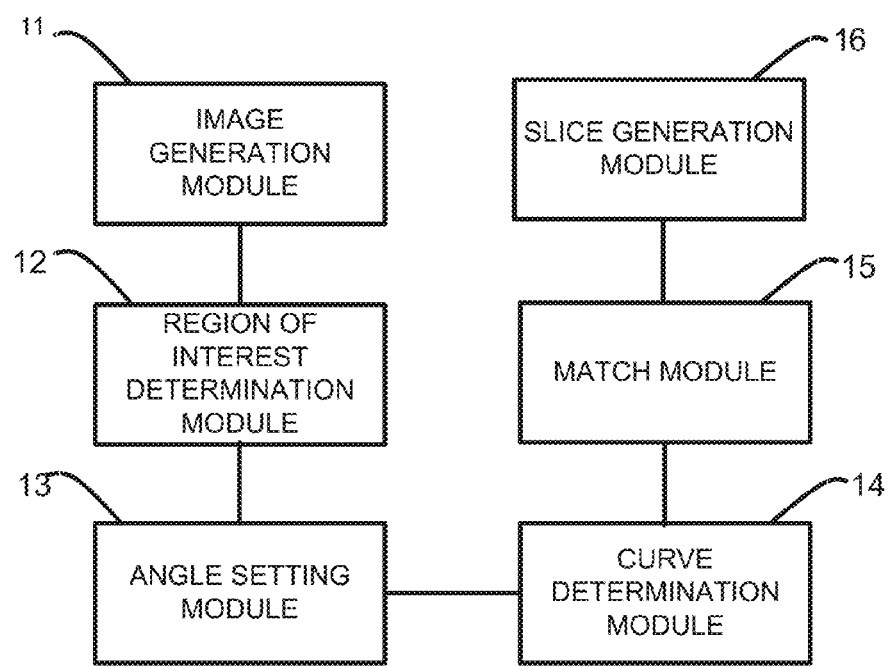
FIG. 1 is a block diagram of a system for generating a CT slice image provided by one embodiment of the present invention.

FIG. 1 is a block diagram of a system for generating a CT slice image provided by one embodiment of the present invention. As shown in FIG. 1, the system comprises an MIP image generation module 11, a region of interest determination module 12, an angle setting module 13, a curve determination module 14, a match module 15 and a slice generation module 16.

The MIP image generation module 11 is used for generating a sagittal MIP image and a coronal MIP image of a reconstructed three-dimensional image. Said "reconstructed three-dimensional image" refers to a three-dimensional reconstructed image of a scanned object obtained by performing image reconstruction on data obtained in scanning. The "coronal MIP image" refers to a two-dimensional projected image formed by projecting pixels having maximum intensity in the above reconstructed three-dimensional image onto a coronal two-dimensional plane, and the "sagittal MIP image" refers to a two-dimensional projected image formed by projecting pixels having maximum intensity in the above reconstructed three-dimensional image onto a sagittal two-dimensional plane. An MIP image is a common sense in the field of medical scanning diagnosis, and its description will be omitted here.

The region of interest determination module 12 is used for determining an image range in an original slice of the reconstructed three-dimensional image, and determining the parts of the sagittal MIP image and the coronal MIP image within the image range as a first region of interest and a second region of interest respectively.

In the clinical diagnosis for backbone, a doctor is only interested in the intervertebral disc and the vertebras connected between the top and bottom of the intervertebral disc. Therefore, regions of interest are determined in the coronal MIP image and the sagittal MIP image by the region of interest determination module 12, avoiding a waste in resource caused by data processing for the whole image.

Figure 2:
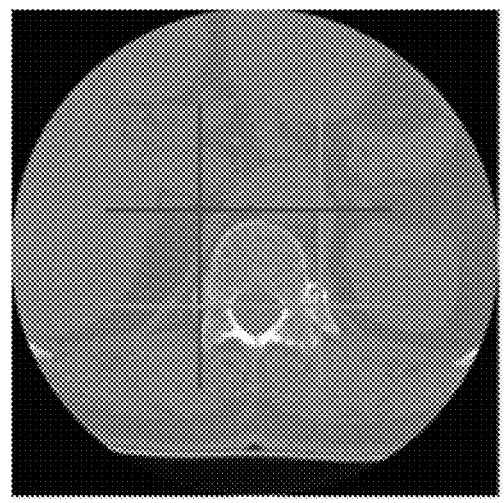
FIG. 2 is a schematic diagram of determining an image range in an original slice in one embodiment of the present invention.

FIG. 2 is a schematic diagram of determining an image range in an original slice in one embodiment of the present invention. As shown in FIG. 2, as an illustration, said image range refers to a range determined by the four straight lines in FIG. 2. Said "original slice" refers to a slice obtained directly by an axial scanning, or a slice obtained in the reconstructed three-dimensional image without adjustment for the angle and position range in accordance with the embodiments of the present invention.

Optionally, the image range determined in the original slice by the region of interest determination module 12 includes a coronal image range and a sagittal image range. The MIP image generation module 11 is also used for generating an axial MIP image of the reconstructed three-dimensional image. Said "axial MIP image" refers to an image obtained by performing MIP on the three-dimensional image to project it onto the horizontal plane (parallel with the cross section of the human body).

Figure 3:
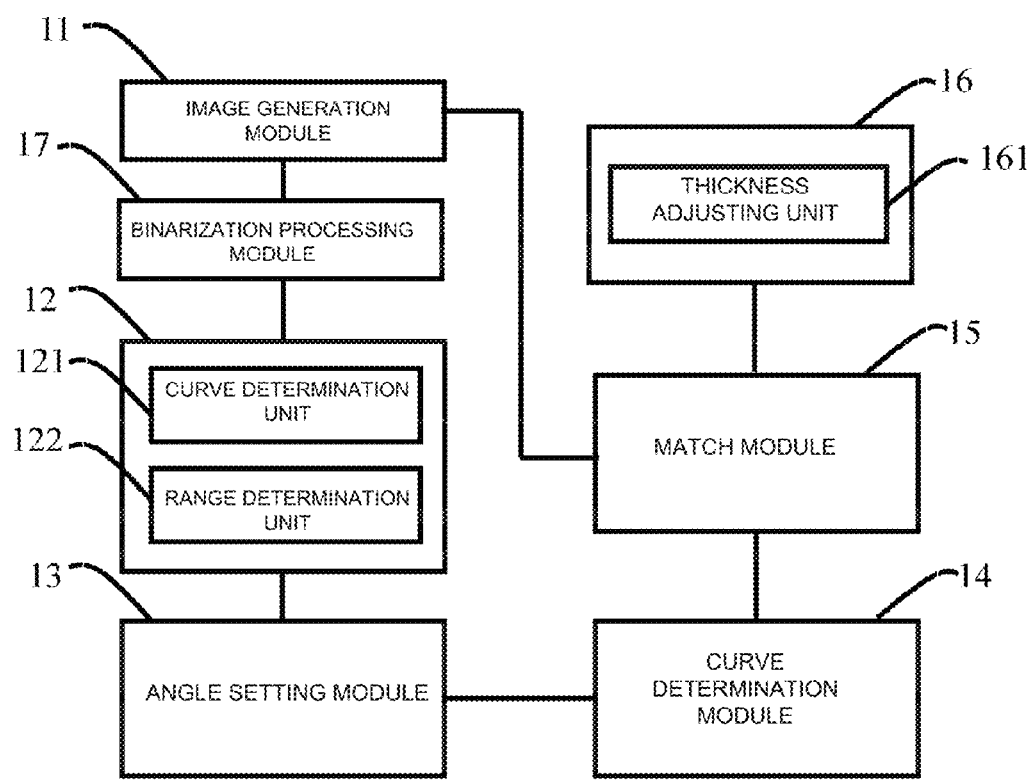
FIG. 3 is a block diagram of a system for generating a CT slice image provided by another embodiment of the present invention.
Figure 4:
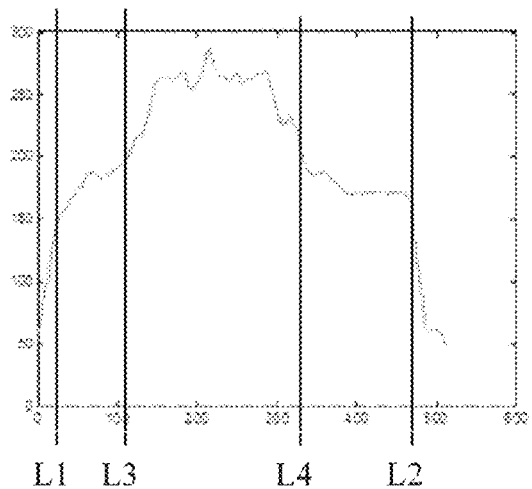
FIG. 4 illustrates a two-dimensional projected curve of an axial MIP image obtained in one embodiment of the present invention.

FIG. 3 is a block diagram of a system for generating a CT slice image provided by another embodiment of the present invention. FIG. 4 illustrates a two-dimensional projected curve of an axial MIP image obtained in one embodiment of the present invention. As shown in FIG. 3, the region of interest determination module 12 further includes a curve determination unit 121 and a range determination unit 122. The curve determination unit 121 is used to form a two-dimensional projected curve of the axial MIP image as shown in FIG. 4, to represent maximum CT values of columns of pixels distributed along a horizontal axis (an axis extending along the left-right direction of the human body when performing CT scan, X axis) of the axial MIP image.

The range determination unit 122 is used to determine an image range at the horizontal axis (an axis extending along the left-right direction of the human body) of the original slice based on the features of the two-dimensional projected curve of said axial MIP image as said coronal image range.

Optionally, when determining the coronal image range, the range determination unit 122 is used to select a part whose curve value is higher than a first preset threshold in the two-dimensional projected curve of the axial MIP image as a first curve range, and to select an image range corresponding to the first curve range on the horizontal axis of the original slice as said coronal image range. For example, the range determination unit 122 makes the part higher than one half of the maximum curve value (first preset threshold, the part whose longitudinal axis value is equal to or more than 150 as shown in FIG. 4) as the first curve range (the range between the vertical lines L1 and L2 as shown in FIG. 4).

Furthermore, when determining the coronal image range, the range determination unit 122 is also used to weight curves within the above first curve range and select a part of the weighted curve whose curve value is larger than a second preset threshold as a second curve range, and to select an image range corresponding to the second curve range on the horizontal axis of the original slice as said coronal image range.

For instance, the range determination unit 122 weights the curve values within the first curve range in accordance with the following Equation (1):

$$N=C/(X-M) \quad (1)$$

wherein X are values of positions of the points on the two-dimensional projected curve at the horizontal axis of the curve, M are values of positions of the midpoints of the curves within the first curve range on the X axis, C are curve values of points on the two-dimensional projected curve, i.e., values at the longitudinal axis of the curve, and N is the weighted curve value.

The range determination unit 122 further makes the part whose weighted curve value is higher than two thirds of its maximum value (e.g., the part whose curve value is larger than 200 in FIG. 4, second preset threshold) as the second curve range (e.g., the range between the two vertical lines L3-L4 in FIG. 4) and selects the range corresponding to the second curve range on the horizontal axis of the original slice as the coronal image range.

Figure 5:
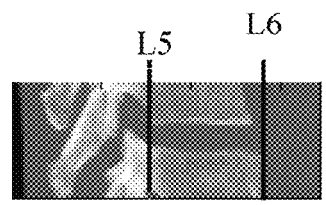
FIG. 5 illustrates a sagittal MIP image obtained in one embodiment of the present invention.

FIG. 5 illustrates a sagittal MIP image obtained in one embodiment of the present invention. As shown in FIG. 5, said MIP image generation module 11 performs sagittal MIP on the reconstructed three-dimensional image within the coronal image range to generate the sagittal MIP image. In other words, the axial MIP image is produced by performing MIP on the whole image of the whole reconstructed three-dimensional image, while the sagittal MIP image as shown in FIG. 5 is produced by performing projection on the three-dimensional image within the coronal image range.

Figure 6:
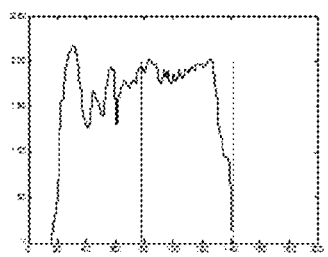
FIG. 6 is a two-dimensional projected curve of a sagittal MIP image obtained in one embodiment of the present invention.

FIG. 6 is a two-dimensional projected curve of a sagittal MIP image obtained in one embodiment of the present invention. As shown in FIG. 6, optionally, when determining the sagittal image range, the curve determination unit 121 is also used to generate the two-dimensional projected curve of the sagittal MIP image to represent maximum CT values of columns of pixels of the sagittal MIP image distributed along its horizontal axis (an axis extending along the back-forth direction of the human body when performing CT scan, Y axis).

The range determination unit 122 is further used to select an image range corresponding to a specific portion of the two-dimensional projected curve of the sagittal MIP image at the longitudinal axis (the axis extending along the back-forth direction of the human body) of the original slice as the above sagittal image range. For example, the image determination unit 122 selects an image range corresponding to a right half part of its two-dimensional projected curve as shown in FIG. 6 in the sagittal MIP image as shown in FIG. 5 as the sagittal image range (i.e., the range between the two vertical lines L5-L6 in FIG. 5), and correspondingly determines the sagittal image range (i.e., the range defined by the two horizontal lines in FIG. 2) in the original slice as shown in FIG. 2.

According to the above descriptions, after determining the image range, the region of interest determination module 12 determines the parts of the sagittal MIP image and the coronal MIP image within the determined image range as a first region of interest and a second region of interest respectively.

Figure 7:
FIG. 7 illustrates a coronal MIP image obtained in one embodiment of the present invention.

FIG. 7 illustrates a coronal MIP image obtained in one embodiment of the present invention. As shown in FIG. 7, the MIP image generation module 11 performs coronal MIP on the reconstructed three-dimensional image within said coronal image range and said sagittal image range to generate the above coronal MIP image. Therefore, the coronal MIP image as shown in FIG. 7 may be used as the coronal region of interest directly, i.e., second region of interest. A waste in resource caused by performing coronal MIP on the whole reconstructed three-dimensional image is avoided.

Figure 5A:
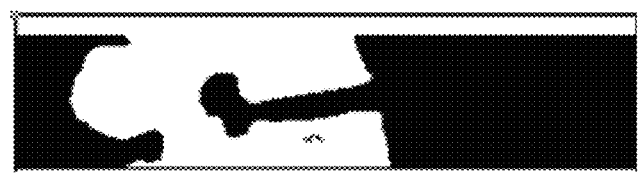
FIG. 5A is an image after binarization processing the sagittal MIP image as shown in FIG. 5.
Figure 7A:
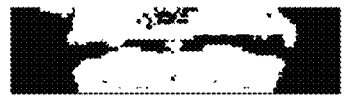
FIG. 7A is an image after binarization processing the coronal MIP image as shown in FIG. 7.

Furthermore, the system for generating a CT slice image of the present invention also comprises a binarization processing module 17 for binarization processing said sagittal MIP image and said coronal MIP image. The curve determination unit 121 is used for generating a plurality of first two-dimensional projected curves of the first region of interest in the binarization processed sagittal MIP image, and further used for generating a plurality of second two-dimensional projected curves of the second region of interest in the binarization processed coronal MIP image. As shown in FIG. 5A, it is an image after binarization processing the sagittal MIP image in FIG. 5. As shown in FIG. 7A, it is an image after binarization processing the coronal MIP image in FIG. 7.

In the following, how to determine the slice position range and the slice angle based on the first region of interest and the second region of interest will be described:

The angle setting module 13 is used for rotating the first region of interest to a plurality of first specific angles for a plurality of times, e.g., continuously rotating the first region of interest to have different angles within the angle range of −20°~+20°.

Figure 8:
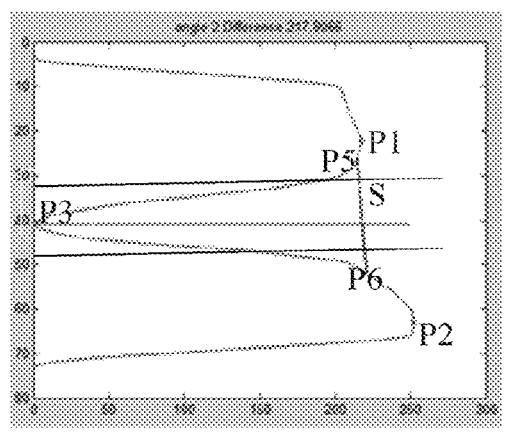
FIG. 8 illustrates one first two-dimensional projected curve obtained in one embodiment of the present invention.

The curve determination module 14 is used to generate a plurality of first two-dimensional projected curves of the first region of interest for said plurality of first specific angles. FIG. 8 illustrates one first two-dimensional projected curve obtained in the embodiment of the present invention. As shown in FIG. 8, each first two-dimensional projected curve represents maximum CT values of columns of pixels of the first region of interest distributed along a longitudinal axis (i.e., an axis distributed up-down along the human body when performing CT scan, Z axis) of an image (sagittal MIP image) on which the first region of interest resides, i.e., the independent variable of the first two-dimensional projected curve is the positions of pixel columns distributed at the longitudinal axis, and the dependent variable of the first two-dimensional projected curve is the maximum CT value of the column of pixels. As shown in FIG. 8, the features of the first two-dimensional projected curve may be used to characterize the features of the first region of interest. For example, in the middle part of the longitudinal axis, the curve value is smaller, corresponding to the soft tissue portion of the first region of interest (whose CT value is smaller); while in the part of the two sides of the longitudinal axis, the curve value is larger, corresponding to the vertebra portion of the first region of interest (whose CT value is larger).

Figure 9:
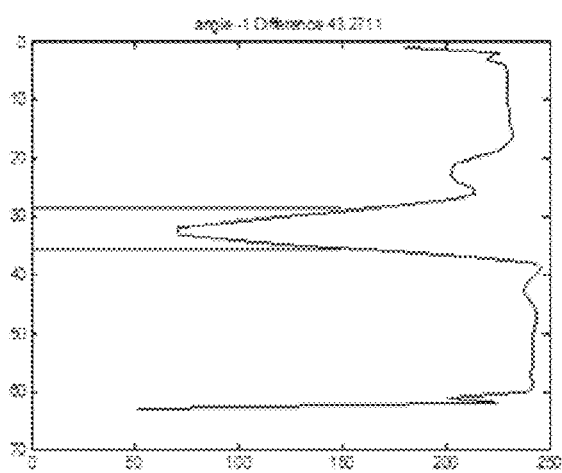
FIG. 9 illustrates one second two-dimensional projected curve obtained in one embodiment of the present invention.

Similarly, the angle setting module 13 is further used to rotate the second region of interest to a plurality of second specific angles for a plurality of times. FIG. 9 illustrates one second two-dimensional projected curve obtained in the embodiment of the present invention. Similar to the first two-dimensional projected curve in principles, the curve determination module 14 is also used to generate a plurality of second two-dimensional projected curves of the second region of interest for the above plurality of second specific angles. Each second two-dimensional projected curve represents maximum CT values of columns of pixels of the second region of interest distributed along a longitudinal axis (i.e., an axis distributed up-down along the human body when performing CT scan, Z axis) of an image (coronal MIP image) on which the second region of interest resides, i.e., the independent variable of the second two-dimensional projected curve is the positions of pixel columns distributed at the longitudinal axis, and the dependent variable of the second two-dimensional projected curve is the maximum CT value of the column of pixels.

The match module 15 is used for respectively selecting a first two-dimensional projected curve and a second two-dimensional projected curve matching with a part to be diagnosed based on the features of the formed plurality of first two-dimensional projected curves and the formed plurality of second two-dimensional projected curves as a first matched curve and a second matched curve. For example, based on the features of the two-dimensional projected curve of the region of interest at each angle, the match module 15 selects a two-dimensional projected curve that matches with the features of the intervertebral disc best as the matched curve.

Optionally, the features of each first two-dimensional projected curve and each second two-dimensional projected curve include a first feature and a second feature. The first feature comprises a lowest point between two wave crests that are farthest with each other, e.g., the lowest point P3 between the wave crests P1 and P2 in FIG. 8. The second feature comprises two feature points (e.g., wave crests P5, P6 in FIG. 8) distributed at two sides of the lowest point respectively. Said two feature points are two wave crests nearest to the lowest point, or points nearest to the lowest point among those whose variation values of curve slopes are larger than a preset value.

For each of the first two-dimensional projected curves and each of the second two-dimensional projected curves, the match module 15 connects the above two feature points by a straight line and calculates a distance between the lowest point and the straight line as a curve depth (a distance between the lowest point P3 and the straight line S as shown in FIG. 8). In addition, the match module 15 is further used to select one with a largest curve depth among the first two-dimensional projected curves as the first matched curve, and to select one with a largest curve depth among the second two-dimensional projected curves as the second matched curve.

Optionally, the MIP image generation module 11 generates said coronal MIP image by performing coronal MIP on the reconstructed three-dimensional image within said coronal and sagittal image ranges at a first specific angle corresponding to the first matched curve.

In the embodiments of the present invention, other features may also be assigned to the first two-dimensional projected curves and the second two-dimensional projected curves according to the specific features of the part to be diagnosed, and curve matching may be performed based on said features.

The slice generation module 16 is used for determining a slice position range and a slice angle based on the features of the first matched curve and a first specific angle corresponding to the first matched curve and based on the features of the second matched curve and a second specific angle corresponding to the second matched curve, and generating a slice in the reconstructed three-dimensional image within the determined slice position range at the determined slice angle.

Optionally, the slice generation module 16 selects one region (a region between the two straight lines as shown in FIG. 8) between the two feature points of the first matched curve or selects one region (a region between the two straight lines as shown in FIG. 9) between the two feature points of the second matched curve, and determines the part corresponding to the selected region in the reconstructed three-dimensional image as the slice position range. For example, when generating slices, it may be considered that a soft tissue portion, i.e., intervertebral disc portion is mainly included in the slice position range.

Therefore, when the slice generation module 16 generates slices, the positions of the slices (i.e., the middle two of the four slices) of the soft tissue portion may be arranged within said slice position range, and generates the slices at the above first specific angle in the sagittal position and at said second specific angle in the coronal position. As shown in FIG. 10, they are slice images obtained in accordance with the embodiments of the present invention.

Optionally, said slice generation module further includes a thickness adjusting unit 161 for adjusting a slice thickness. For example, if an initially set slice thickness is so large that the thicknesses of the middle two slices exceed the slice position range, the slice thickness may be re-set by the thickness adjusting unit 161 such that within the slice position range, it is avoided that the obtained slices do not satisfy the clinical diagnosis requirements. For example, the obtained middle slices contain bone tissue features.

Figure 11:
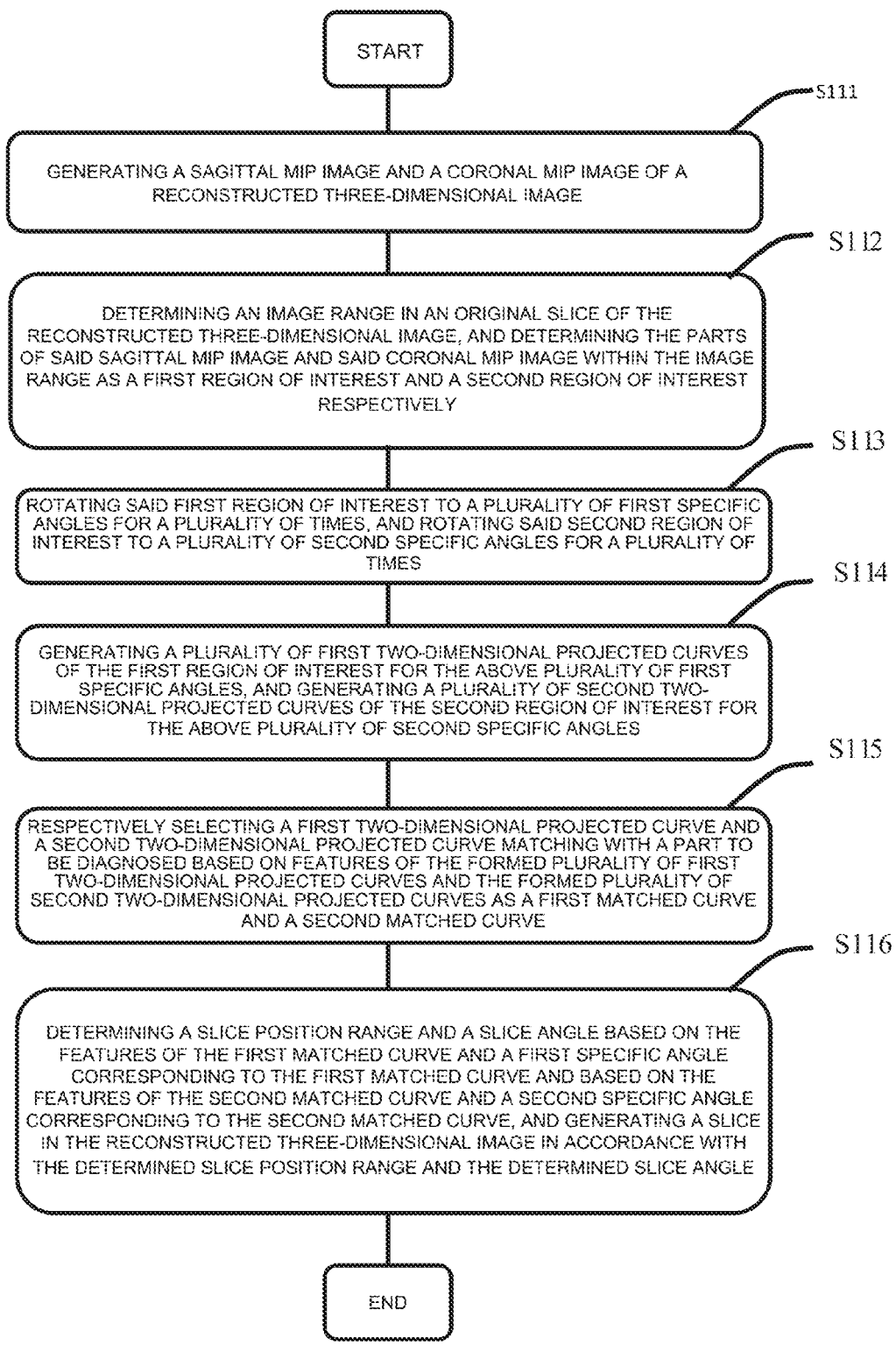
FIG. 11 is a flow chart of a method for generating a CT slice image provided by one embodiment of the present invention.

FIG. 11 is a flow chart of a method for generating a CT slice image provided by one embodiment of the present invention. As shown in FIG. 11, the method comprises an MIP image generating step S111, a region of interest determining step S112, an angle setting step S113, a curve determining step S114, a matching step S115 and a slice generating step S116.

MIP image generating step S111: generating a sagittal MIP image and a coronal MIP image of a reconstructed three-dimensional image. For example, the MIP image generating step S111 comprises: a step of generating a sagittal MIP image as shown in FIG. 5, and a step of generating a coronal MIP image as shown in FIG. 7.

Region of interest determining step S112: determining an image range in an original slice of the reconstructed three-dimensional image, and determining the parts of said sagittal MIP image and said coronal MIP image within the image range as a first region of interest and a second region of interest respectively. For example, the region of interest determining step S112 determines the range defined by the four straight lines on the original slice as shown in FIG. 2 as the image range, and further defines a first region of interest in the sagittal MIP image as shown in FIG. 5 and defines a second region of interest in the coronal MIP image as shown in FIG. 7 based on the image range, in which the range defined by the two vertical lines is the coronal image range, and the range defined by the two horizontal lines is the sagittal image range.

Angle setting step S113: rotating said first region of interest to a plurality of first specific angles for a plurality of times, and rotating said second region of interest to a plurality of second specific angles for a plurality of times.

Curve determining step S114: generating a plurality of first two-dimensional projected curves of the first region of interest for the above plurality of first specific angles, and generating a plurality of second two-dimensional projected curves of the second region of interest for the above plurality of second specific angles, each first two-dimensional projected curve representing maximum CT values of columns of pixels of the first region of interest distributed along a longitudinal axis of an image on which the first region of interest resides, each second two-dimensional projected curve representing maximum CT values of columns of pixels of the second region of interest distributed along a longitudinal axis of an image on which the second region of interest resides. For example, the curve determining step S114 generates the first two-dimensional projected curve as shown in FIG. 8 for each first specific angle, and generates the second two-dimensional projected curve as shown in FIG. 9 for each second specific angle.

Matching step S115: respectively selecting a first two-dimensional projected curve and a second two-dimensional projected curve matching with a part to be diagnosed based on features of the formed plurality of first two-dimensional projected curves and the formed plurality of second two-dimensional projected curves as a first matched curve and a second matched curve.

Slice generating step S116: determining a slice position range and a slice angle based on the features of the first matched curve and a first specific angle corresponding to the first matched curve and based on the features of the second matched curve and a second specific angle corresponding to the second matched curve, and generating a slice in the reconstructed three-dimensional image in accordance with the determined slice position range and the determined slice angle.

Optionally, the features of each first two-dimensional projected curve and each second two-dimensional projected curve include a lowest point between two wave crests that are farthest with each other and two feature points at two sides of said lowest point respectively. Said two feature points are: two wave crests nearest to the lowest point, or points whose curve slopes vary such that the variation is greater than a preset value.

The matching step S115 comprises the following steps:

for each of the first two-dimensional projected curves and each of the second two-dimensional projected curves, connecting said two feature points by a straight line and calculating a distance between the lowest point and the straight line as a curve depth; and selecting one with a largest curve depth among the first two-dimensional projected curves as the first matched curve, and selecting one with a largest curve depth among the second two-dimensional projected curves as the second matched curve.

Furthermore, the MIP image generating step S111 further comprises: generating an axial MIP image of the reconstructed three-dimensional image.

Figure 12:
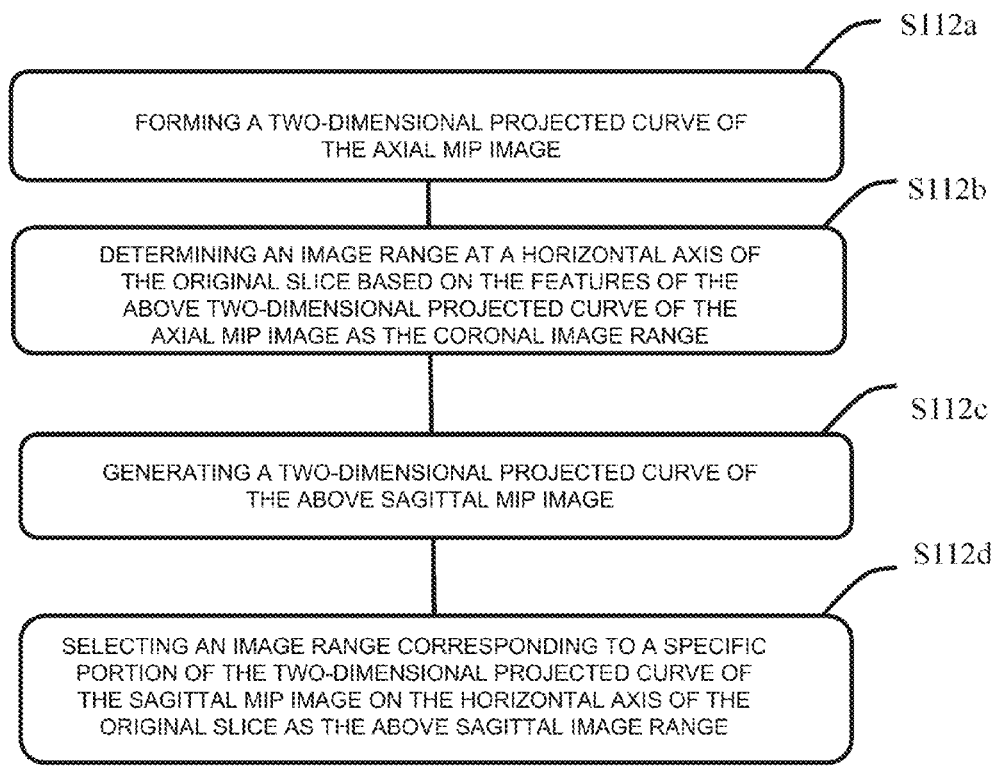
FIG. 12 illustrates a flow chart of determining an image range in Step S112 in FIG. 11.
Figures 13D, 13E:
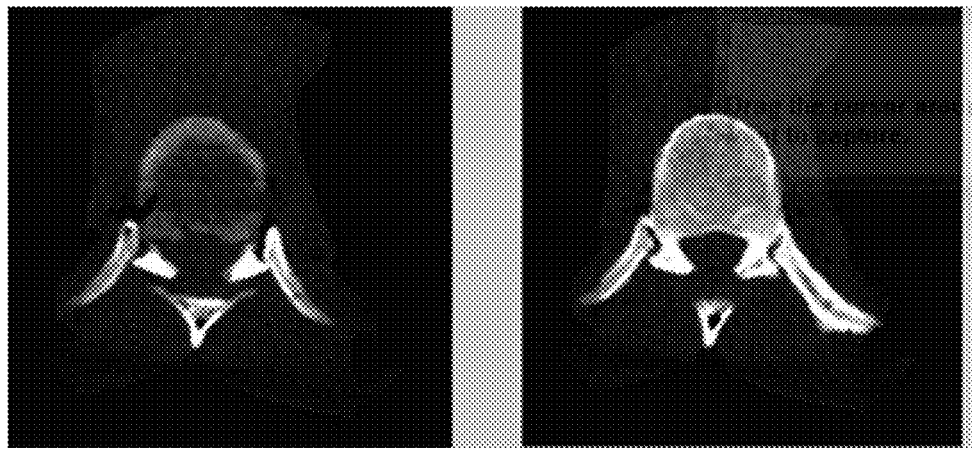
FIG. 13D shows a slice image with more vertebra tissue features, obtained in one embodiment of the present invention.
FIG. 13E shows a slice image of a disc portion with higher contrast, obtained in one embodiment of the present invention.
Figure 14A:
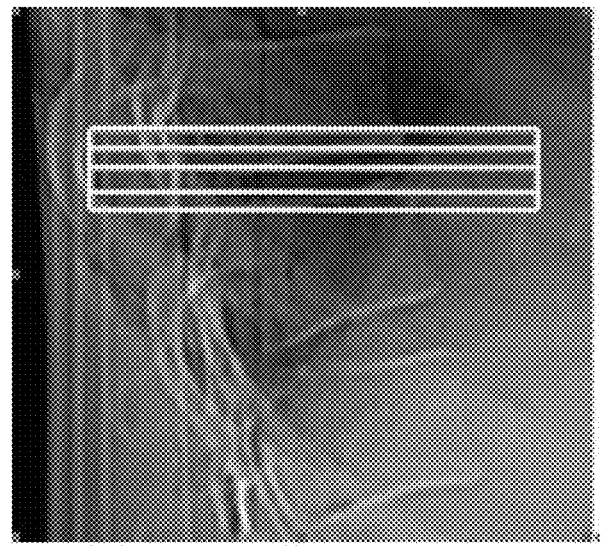
FIG. 14A shows an image of a disc with an inappropriate angle parameter, obtained in one embodiment of the present invention.
Figure 15:
FIG. 15 shows a spine image with scoliosis, obtained in one embodiment of the present invention.
Figure 16A:
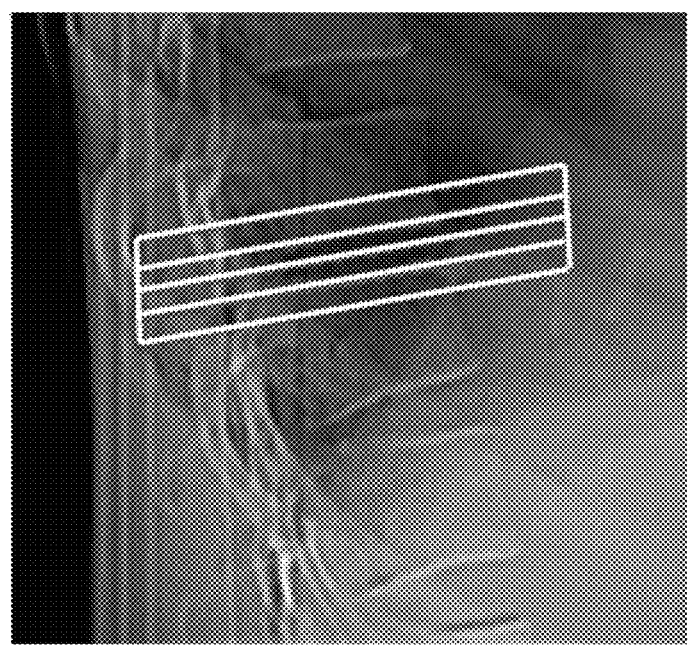
FIG. 16A shows an image with an inappropriate thickness parameter, obtained in one embodiment of the present invention.
Figure 16B:
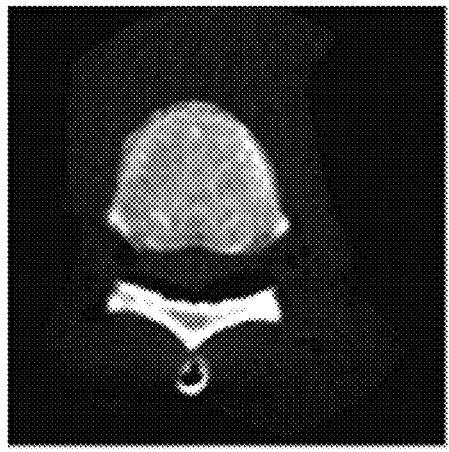
FIG. 16B shows a slice image with soft tissue features, obtained in one embodiment of the present invention.
Figure 16C:
FIG. 16C shows a slice image with soft tissue features due to an inappropriate thickness parameter, obtained in one embodiment of the present invention.
Figure 16D:
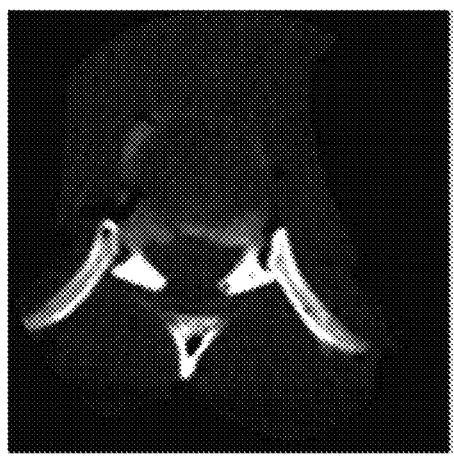
FIG. 16D shows a slice image of a disc portion with soft tissue features, obtained in one embodiment of the present invention.
Figure 16E:
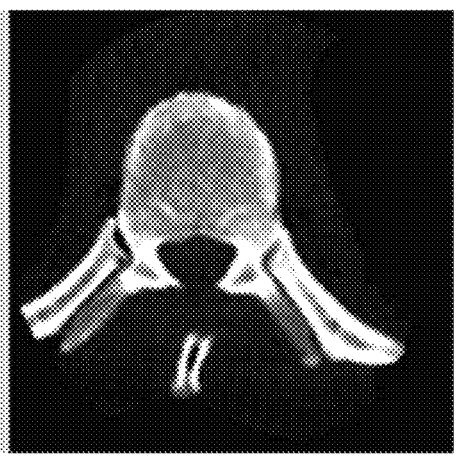
FIG. 16E shows a slice image of a disc portion, obtained in one embodiment of the present invention.

FIG. 12 is a flow chart of "determining an image range in an original slice of the reconstructed three-dimensional image" in FIG. 11. As shown in FIG. 12, in the region of interest determining step S112, the "determining an image range in an original slice of the reconstructed three-dimensional image" specifically comprises:

Step S112A: forming a two-dimensional projected curve of said axial MIP image, to represent maximum CT values of columns of pixels distributed along a horizontal axis of the axial MIP image. For example, Step S112A performs a projection on the axial MIP image to form a two-dimensional projected curve as shown in FIG. 4.

Step S112B: determining an image range at a horizontal axis of the original slice based on the features of the two-dimensional projected curve of said axial MIP image as the coronal image range, in which in the MIP image generating step S111, said sagittal MIP image is generated by performing a sagittal MIP on the reconstructed three-dimensional image within the coronal image range.

Step S112C: generating a two-dimensional projected curve of the above sagittal MIP image, to represent maximum CT values of columns of pixels of the sagittal MIP image distributed along its horizontal axis. For example, Step S112C performs a projection on the sagittal MIP image as shown in FIG. 5 to generate a two-dimensional projected curve as shown in FIG. 6.

Step S112D: selecting an image range corresponding to a specific portion of the two-dimensional projected curve of the sagittal MIP image on the horizontal axis of the original slice as the above sagittal image range. In the MIP image generating step S111, said coronal MIP image is generated by performing coronal MIP on the reconstructed three-dimensional image within the coronal and sagittal image ranges at a first specific angle corresponding to the first matched curve.

Step S112B further comprises: selecting a part whose curve value is higher than a first preset threshold in the two-dimensional projected curve of the axial MIP image as a first curve range, and selecting an image range corresponding to the first curve range on the horizontal axis of the original slice as said coronal image range.

Optionally, Step S112B further comprises: weighting curves within the above first curve range and selecting a part of the weighted curve whose curve value is larger than a second preset threshold as a second curve range, and selecting an image range corresponding to the second curve range on the horizontal axis of the original slice as said coronal image range.

Optionally, the method for generating a CT slice image of the present invention further comprises a binarization processing step after the MIP image generating step S111: binarization processing the sagittal MIP image and the coronal MIP image generated in Step S111. Said plurality of first two-dimensional projected curves are generated by performing a two-dimensional projection on the first region of interest in the binarization processed sagittal MIP image; and said plurality of second two-dimensional projected curves are generated by performing a two-dimensional projection on the second region of interest in the binarization processed coronal MIP image.

Optionally, the slice generating step S116 comprises: selecting one region between two feature points of the first matched curve or selecting one region between two feature points of the second matched curve, and determining the part corresponding to the selected region in the reconstructed three-dimensional image as the slice position range.

Optionally, after the slice generating step S116, the method for generating a CT slice image of the present invention further comprises: adjusting a slice thickness.

A process for generating slice images of intervertebral disc will be described by examples in the following. It should be noted that said examples are only illustrated for better understanding the present invention, and are not intended to limit the contents of the present invention.

First step: generating an axial MIP image of a reconstructed three-dimensional image of a backbone, and obtaining a two-dimensional projected curve of the axial MIP image, e.g., the curve as shown in FIG. 4, the independent variable (horizontal axis, corresponding to the horizontal axis of the cross section) of the curve representing a position of a pixel column, and the dependent variable (longitudinal axis, corresponding to the longitudinal axis of the cross section) of the curve representing a maximum CT value in the pixel column.

Second step: making the part that is higher than a maximum curve value, higher than 100 in the two-dimensional projected curve of the axial MIP image as a first curve range, e.g., the range between the vertical lines L1 and L2 as shown in FIG. 4.

Third step: weighting the curve values within the first curve range using Equation (1), and making the part whose weighted curve value is higher than 200 as a second curve range, e.g., the range between the two vertical lines L3-L4 in FIG. 4.

Fourth step: selecting a range corresponding to the second curve range on the horizontal axis of the original slice image as shown in FIG. 2 as a coronal image range.

Fifth step: performing sagittal MIP on the part in the reconstructed three-dimensional image within the coronal image range to produce a sagittal MIP image as shown in FIG. 5.

Sixth step: binarization processing the sagittal MIP image as shown in FIG. 5 to obtain a binarized sagittal MIP image as shown in FIG. 5.

Seventh step: obtaining a two-dimensional projected curve of the binarized image as shown in FIG. 5, e.g., the curve as shown in FIG. 6, in which the independent variable (horizontal axis, corresponding to the horizontal axis of the sagittal section) is a position of a pixel column, and the dependent variable (longitudinal axis, corresponding to the longitudinal axis of the sagittal section) is a maximum CT value in the pixel column.

Eighth step: determining the horizontal axis coordinate of the right half part in the curve as shown in FIG. 6.

Ninth step: selecting an image range corresponding to the horizontal axis coordinate of the right half part of the curve at the longitudinal axis of the original slice as shown in FIG. 2 as a sagittal image range, i.e., the range between the two horizontal lines in FIG. 2.

Tenth step: determining the part in the sagittal MIP image in FIG. 5 or FIG. 5A within the sagittal image range (i.e., the range between the two vertical lines L5-L6) as a sagittal region of interest (first region of interest).

Eleventh step: within a range of −20°~+20°, rotating the sagittal region of interest to a plurality of angles, and generating a two-dimensional projected curve of the sagittal region of interest for each angle (first two-dimensional projected curve as shown in FIG. 8).

Twelfth step: selecting a two-dimensional projected curve of the sagittal region of interest with the largest curve depth as a sagittal matched curve.

Thirteenth step: determining the angle corresponding to the sagittal matched curve as a sagittal slice angle.

Fourteenth step: performing coronal MIP on the part of the reconstructed three-dimensional image within the coronal image range and the sagittal image range at the above sagittal slice angle to generate the coronal MIP image as shown in FIG. 7 (in the present example, since the coronal MIP image as shown in FIG. 7 is a projected image of the part of the reconstructed three-dimensional image within the coronal and sagittal image ranges, said image is used as the coronal region of interest directly, i.e., the part of the coronal MIP image within the image range).

Fifteenth step: binarization processing the coronal region of interest as shown in FIG. 7 to obtain a binarized image as shown in FIG. 7A.

Sixteenth step: performing a two-dimensional projection on the binarized image as shown in FIG. 7A to obtain a coronal two-dimensional projected curve as shown in FIG. 9.

Seventeenth step: selecting a coronal two-dimensional projected curve with the largest curve depth as a coronal matched curve.

Eighteenth step: determining the angle corresponding to the coronal matched curve as a coronal slice angle.

Nineteenth step: selecting one region (a region between the two straight lines as shown in FIG. 8) between two feature points of the coronal matched curve or selecting one region (a region between the two straight lines as shown in FIG. 9) between two feature points of the sagittal matched curve, and determining the part corresponding to the selected region in the reconstructed three-dimensional image as a slice position range.

Figure 10A:
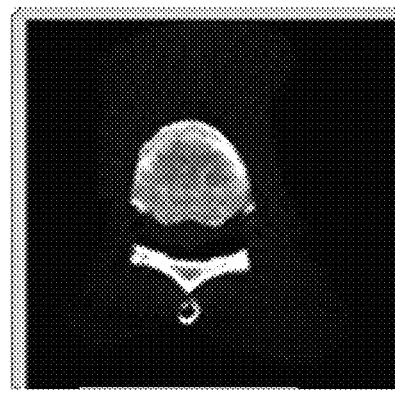
FIG. 10A shows a slice image of a disc portion, obtained in one embodiment of the present invention.
Figure 10B:
FIG. 10B shows a slice image of sagittal slice angle, obtained in one embodiment of the present invention.
Figure 10C:
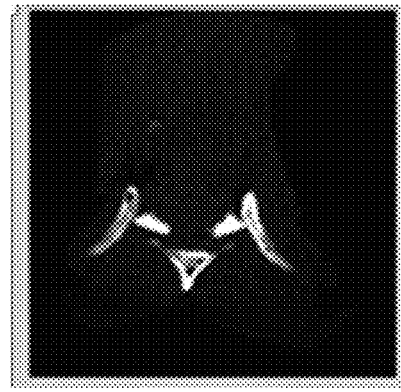
FIG. 10C shows a slice image of a coronal slice angle, obtained in one embodiment of the present invention.
Figure 10D:
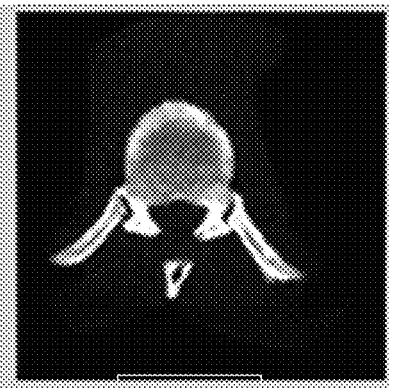
FIG. 10D shows a slice image of a disc portion, obtained in one embodiment of the present invention.

Twentieth step: generating two slice images (images as shown in FIG. 10B and FIG. 10C) within the slice position range at the sagittal slice angle and the coronal slice angle, and generating two additional slice images (images as shown in FIG. 10A and FIG. 10D) at two sides of said two slices respectively, said two slice images being regarded as images of the intervertebral disc portion, said two additional slice images being regarded as images of the vertebra portions connected between the top and bottom of the intervertebral disc respectively.

In the system and method for generating a CT slice image provided by the embodiments of the present invention, by generating a sagittal MIP image and a coronal MIP image, regions of interest are determined in the generated sagittal MIP image and the generated coronal MIP image respectively, the regions of interest are rotated and two-dimensional projected curves of the regions of interest are obtained, and a position range and angle matching with a part to be diagnosed best are determined as a slice position range and a slice angle via features of the two-dimensional projected curves of the regions of interest, the appropriate slice position range and angle are determined, so that the generated slice can satisfy the requirements for the clinical diagnosis, thus avoiding a problem on slice image due to posture changes during scanning or restrictions of the machine itself, avoiding a problem on slice image due to inappropriate parameter settings in posterior reconstruction, significantly improving the working efficiency of the CT scan diagnosis, and avoiding an increase in the patent's scanning dose.

Some exemplary embodiments have been described in the above. However, it should be understood that various modifications may be made thereto. For example, if the described techniques are carried out in different orders, and/or if the components in the described system, architecture, apparatus or circuit are combined in different ways and/or replaced or supplemented by additional components or equivalents thereof, proper results may still be achieved. Accordingly, other embodiments are also falling within the protection scope of the claims.

We claim:

1. A system for generating a CT slice image, comprising:
an MIP image generation module for generating a sagittal MIP image and a coronal MIP image of a reconstructed three-dimensional image;
a region of interest determination module for determining an image range in an original slice of the reconstructed three-dimensional image, and determining the parts of the sagittal MIP image and the coronal MIP image within the image range as a first region of interest and a second region of interest respectively;
an angle setting module for rotating the first region of interest to a plurality of first specific angles for a plurality of times, and rotating the second region of interest to a plurality of second specific angles for a plurality of times;
a curve determination module for generating a plurality of first two-dimensional projected curves of the first region of interest for the plurality of first specific angles, and generating a plurality of second two-dimensional projected curves of the second region of interest for the plurality of second specific angles, each first two-dimensional projected curve representing maximum CT values of columns of pixels of the first region of interest distributed along a longitudinal axis of an image on which the first region of interest resides, each second two-dimensional projected curve representing maximum CT values of columns of pixels of the second region of interest distributed along a longitudinal axis of an image on which the second region of interest resides;
a match module for respectively selecting a first two-dimensional projected curve and a second two-dimensional projected curve matching with a part to be diagnosed based on features of the plurality of first two-dimensional projected curves and the plurality of second two-dimensional projected curves as a first matched curve and a second matched curve; and
a slice generation module for determining a slice position range and a slice angle based on the features of the first matched curve and a first specific angle corresponding to the first matched curve and based on the features of the second matched curve and a second specific angle corresponding to the second matched curve, and generating a slice in the reconstructed three-dimensional image in accordance with the determined slice position range and the determined slice angle.

2. The system for generating a CT slice image according to claim 1, wherein the features of each of the first two-dimensional projected curves and each of the second two-dimensional projected curves comprise a lowest point between two wave crests that are farthest with each other and two feature points distributed at two sides of the lowest point respectively;
the two feature points are two wave crests nearest to the lowest point, or points whose curve slopes vary such that the variation is larger than a preset value;
for each of the first two-dimensional projected curves and each of the second two-dimensional projected curves, the match module connects the two feature points by a straight line and calculates a distance between the lowest point and the straight line as a curve depth;
the match module is further used to select one with a largest curve depth among the first two-dimensional projected curves as the first matched curve, and to select one with a largest curve depth among the second two-dimensional projected curves as the second matched curve.

3. The system for generating a CT slice image according to claim 2, wherein the slice generation module selects one region between two feature points of the first matched curve or selects one region between two feature points of the second matched curve, and determines a part in the reconstructed three-dimensional image corresponding to the selected region as the slice position range.

4. The system for generating a CT slice image according to claim 3, wherein the slice generation module further comprises: a thickness adjusting unit for adjusting a slice thickness.

5. The system for generating a CT slice image according to claim 1, wherein the image range determined in the original slice of the reconstructed three-dimensional image by the region of interest determination module comprises a coronal image range and a sagittal image range, the MIP image generation module is further used to generate an axial MIP image of the reconstructed three-dimensional image, the region of interest determination module comprising a curve determination unit and a range determination unit;
the curve determination unit is used to form a two-dimensional projected curve of the axial MIP image, to represent maximum CT values of columns of pixels distributed along a horizontal axis of the axial MIP image;
the range determination unit is used to determine an image range at a horizontal axis of the original slice based on features of the two-dimensional projected curve of the axial MIP image as the coronal image range, the MIP image generation module performing a sagittal MIP on the reconstructed three-dimensional image within the coronal image range to generate the sagittal MIP image;
the curve determination unit is further used to generate a two-dimensional projected curve of the sagittal MIP image, to represent maximum CT values of columns of pixels of the sagittal MIP image distributed along its horizontal axis;
the range determination unit is further used to select an image range corresponding to a specific portion of the two-dimensional projected curve of the sagittal MIP image on the horizontal axis of the original slice as the sagittal image range;
the MIP image generation module is to perform coronal MIP on the reconstructed three-dimensional image within the coronal image range and the sagittal image range at a first specific angle corresponding to the first matched curve to generate the coronal MIP image.

6. The system for generating a CT slice image according to claim 5, wherein the range determination unit is used to select a part whose curve value is higher than a first preset threshold in the two-dimensional projected curve of the axial MIP image as a first curve range, and to select an image range corresponding to the first curve range on the horizontal axis of the original slice as the coronal image range.

7. The system for generating a CT slice image according to claim 6, wherein the range determination unit is further used to weight curves within the first curve range and select a part of the weighted curve whose curve value is larger than a second preset threshold as a second curve range, and to select an image range corresponding to the second curve range on the horizontal axis of the original slice as the coronal image range.

8. The system for generating a CT slice image according to claim 5, further comprising a binarization processing module for binarization processing the sagittal MIP image and the coronal MIP image, the curve determination unit being used for generating the plurality of first two-dimensional projected curves of the first region of interest in the binarization processed sagittal MIP image, and further used for generating the plurality of second two-dimensional projected curves of the second region of interest in the binarization processed coronal MIP image.

9. A method for generating a CT slice image, comprising:
an MIP image generating step: generating a sagittal MIP image and a coronal MIP image of a reconstructed three-dimensional image;
a region of interest determining step: determining an image range in an original slice of the reconstructed three-dimensional image, and determining the parts of the sagittal MIP image and the coronal MIP image within the image range as a first region of interest and a second region of interest respectively;
an angle setting step: rotating the first region of interest to a plurality of first specific angles for a plurality of times, and rotating the second region of interest to a plurality of second specific angles for a plurality of times;
a curve determining step: generating a plurality of first two-dimensional projected curves of the first region of interest for the plurality of first specific angles, and generating a plurality of second two-dimensional projected curves of the second region of interest for the plurality of second specific angles, each first two-dimensional projected curve representing maximum CT values of columns of pixels of the first region of interest distributed along a longitudinal axis of an image on which the first region of interest resides, each second two-dimensional projected curve representing maximum CT values of columns of pixels of the second region of interest distributed along a longitudinal axis of an image on which the second region of interest resides;
a matching step: respectively selecting a first two-dimensional projected curve and a second two-dimensional projected curve matching with a part to be diagnosed based on features of the plurality of first two-dimensional projected curves and the plurality of second two-dimensional projected curves as a first matched curve and a second matched curve; and
a slice generating step: determining a slice position range and a slice angle based on the features of the first matched curve and a first specific angle corresponding to the first matched curve and based on the features of the second matched curve and a second specific angle corresponding to the second matched curve, and generating a slice in the reconstructed three-dimensional image in accordance with the determined slice position range and the determined slice angle.

10. The method for generating a CT slice image according to claim 9, wherein the features of each of the first two-dimensional projected curves and each of the second two-dimensional projected curves comprise a lowest point between two wave crests that are farthest with each other and two feature points distributed at two sides of the lowest point respectively;
the two feature points are two wave crests nearest to the lowest point, or points whose curve slopes vary such that the variation is greater than a preset value;
the matching step comprises:

for each of the first two-dimensional projected curves and each of the second two-dimensional projected curves, connecting the two feature points by a straight line and calculating a distance between the lowest point and the straight line as a curve depth; and
selecting one with a largest curve depth among the first two-dimensional projected curves as the first matched curve, and selecting one with a largest curve depth among the second two-dimensional projected curves as the second matched curve.

11. The method for generating a CT slice image according to claim 10, wherein the slice generating step comprises: selecting one region between two feature points of the first matched curve or selecting one region between two feature points of the second matched curve, and determining a part in the reconstructed three-dimensional image corresponding to the selected region as the slice position range.

12. The method for generating a CT slice image according to claim 11, wherein the slice generating step further comprises: adjusting a slice thickness.

13. The method for generating a CT slice image according to claim 9, wherein the image range determined in the original slice of the reconstructed three-dimensional image comprises a coronal image range and a sagittal image range,
the MIP image generating step comprises: generating an axial MIP image of the reconstructed three-dimensional image;
the region of interest determining step comprises:
forming a two-dimensional projected curve of the axial MIP image, to represent maximum CT values of columns of pixels distributed along a horizontal axis of the axial MIP image;
determining an image range at a horizontal axis of the original slice based on features of the two-dimensional projected curve of the axial MIP image as the coronal image range, the MIP image generating step performing a sagittal MIP on the reconstructed three-dimensional image within the coronal image range to generate the sagittal MIP image;
generating a two-dimensional projected curve of the sagittal MIP image, to represent maximum CT values of columns of pixels of the sagittal MIP image distributed along its horizontal axis; and
selecting an image range corresponding to a specific portion of the two-dimensional projected curve of the sagittal MIP image on the horizontal axis of the original slice as the sagittal image range; the coronal MIP image is generated by performing coronal MIP on the reconstructed three-dimensional image within the coronal image range and the sagittal image range at a first specific angle corresponding to the first matched curve.

14. The method for generating a CT slice image according to claim 13, wherein the determining an image range at a horizontal axis of the original slice based on features of the two-dimensional projected curve of the axial MIP image as the coronal image range comprises: selecting a part whose curve value is higher than a first preset threshold in the two-dimensional projected curve of the axial MIP image as a first curve range, and selecting an image range corresponding to the first curve range on the horizontal axis of the original slice as the coronal image range.

15. The method for generating a CT slice image according to claim 14, wherein the determining an image range at a horizontal axis of the original slice based on features of the two-dimensional projected curve of the axial MIP image as the coronal image range further comprises: weighting curves within the first curve range and selecting a part of the weighted curve whose curve value is larger than a second preset threshold as a second curve range, and selecting an image range corresponding to the second curve range on the horizontal axis of the original slice as the coronal image range.

16. The method for generating a CT slice image according to claim 13, wherein the method for generating a CT slice image further comprises a binarization processing step: binarization processing the sagittal MIP image and the coronal MIP image, the plurality of first two-dimensional projected curves being generated by performing two-dimensional curve projection on the first region of interest in the binarization processed sagittal MIP image; the plurality of second two-dimensional projected curves being generated by performing two-dimensional curve projection on the second region of interest in the binarization processed coronal MIP image.

* * * * *